(12) United States Patent
Hynynen et al.

(10) Patent No.: US 6,984,209 B2
(45) Date of Patent: Jan. 10, 2006

(54) HARMONIC MOTION IMAGING

(75) Inventors: Kullervo H. Hynynen, Medfield, MA (US); Elisa Konofagou, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 10/612,555

(22) Filed: Jul. 2, 2003

(65) Prior Publication Data

US 2005/0004466 A1  Jan. 6, 2005

(51) Int. Cl.
*A61B 8/00* (2006.01)

(52) U.S. Cl. ................................ 600/438
(58) Field of Classification Search .......... 600/437, 600/438, 443, 447, 449, 585
See application file for complete search history.

(56) References Cited

U.S. PATENT DOCUMENTS

| | | | | |
|---|---|---|---|---|
| 4,012,950 A | * | 3/1977 | Kompfner et al. | ............ 73/596 |
| 4,566,460 A | * | 1/1986 | Sato et al. | .................. 600/438 |
| 4,610,255 A | * | 9/1986 | Shimura et al. | ............ 600/443 |
| 5,501,655 A | * | 3/1996 | Rolt et al. | ...................... 601/3 |
| 5,592,085 A | * | 1/1997 | Ehman | ........................ 324/309 |
| 5,606,971 A | * | 3/1997 | Sarvazyan | .................. 600/438 |
| 5,810,731 A | * | 9/1998 | Sarvazyan et al. | .......... 600/438 |
| 5,827,204 A | * | 10/1998 | Grandia et al. | ................. 601/2 |
| 5,903,516 A | * | 5/1999 | Greenleaf et al. | ............ 367/92 |
| 5,984,881 A | * | 11/1999 | Ishibashi et al. | ............... 601/2 |
| 6,068,597 A | * | 5/2000 | Lin | ............................. 600/443 |

\* cited by examiner

*Primary Examiner*—Francis J. Jaworski
(74) *Attorney, Agent, or Firm*—Mintz, Levin, Cohn, Ferris, Glovsky and Popeo, P.C.; Ivor R. Elrifi; Shane H. Hunter (57) ABSTRACT

A method of determining a property of a desired region in an object includes transmitting first and second energy beams from first and second sources into the object such that the beams intersect at the desired region to induce vibration of the desired region, transmitting energy from a third source into the desired region, receiving signals from the desired region due to the energy from the third source, and analyzing at least one of amplitude, phase and frequency of the vibration of the desired region indicated by the received signals to determine the property of the desired region.

20 Claims, 8 Drawing Sheets

HARMONIC MOTION IMAGING

STATEMENT AS TO FEDERALLY-SPONSORED RESEARCH

This invention was made at least in part with Government support under Grant No. NIH CA82275, awarded by the National Institutes of Health. The Government has certain rights in this invention.

FIELD OF THE INVENTION

The invention relates to non-invasive imaging and/or therapeutic techniques and more particularly to localized harmonic motion imaging and/or therapy.

BACKGROUND OF THE INVENTION

To help diagnose cancers and to help determine therapeutic strategies, it is useful to detect and locate potentially-tumorous tissues. Locating tumor tissue may involve determining mechanical properties of tissue because mechanical properties of tumor tissue are known to differ from mechanical properties of non-tumorous tissue. For example, the elastic modulus (a measure of force needed to deform a material by a certain amount, and thus a measure of the tissue's stiffness) differs between tumorous tissue and surrounding, non-tumorous tissue. To determine the elastic modulus of tissue, stimuli may be applied to the tissue and elasticity determined, e.g., by measuring induced strain, tissue displacement, or Doppler shifts.

To help determine mechanical properties of tissue, the tissue may be vibrated remotely, using dual ultrasound beams, and mechanical properties of the tissue measured. As an ultrasound beam propagates through tissue, its momentum changes, e.g., due to absorption and scatter of the beam. Momentum changes result in a radiation force acting on the tissue through which the beam propagates. Using beams with different frequencies, $f_1$ and $f_2$, that intersect at a focal region, a wave of varying force is produced that is amplitude modulated at a difference frequency $f_d = f_1 - f_2$, producing tissue motion. The magnitude of the tissue motion depends on the radiation force applied and the mechanical properties of the tissue. It has been suggested that this tissue motion produces an acoustic wave that propagates, possibly through other tissue, and that can be detected by an external hydrophone. Such a detected signal is dependent on at least the mechanical and acoustic properties of the tissue at the focal region and the tissue between the focal region and the hydrophone, the resonance characteristics of the hydrophone housing and its surroundings, and interactions at the hydrophone. Thus, significant noise may be introduced and may affect determination of the mechanical properties of the tissue at the focal region when the method described above is used.

SUMMARY OF THE INVENTION

In general, in an aspect, the invention provides a method of determining a property of a desired region in an object, the method including transmitting first and second energy beams from first and second sources into the object such that the beams intersect at the desired region to induce vibration of the desired region, transmitting energy from a third source into the desired region, receiving signals from the desired region due to the energy from the third source, and analyzing at least one of amplitude, phase and frequency of the vibration of the desired region indicated by the received signals to determine the property of the desired region.

Implementations of the invention may include one or more of the following features. The analyzing comprises analyzing the amplitude of the vibration and at least one of the frequency and the phase of the vibration. The first and second energy beams have first and second frequencies, respectively, that are different from each other. The analyzing determines a value related to a mechanical property of the desired region or a parameter that is related to the mechanical property of the desired region. The value is related to a stiffness/elasticity of the desired region. The analyzing comprises cross-correlating multiple received signals. The energy from the sources is ultrasound energy and the energy from the third source is one of a plurality of ultrasound pulses and a plurality of ultrasound bursts.

In general, in another aspect, the invention provides a system for determining a property of a desired region in an object, the system including first, second, and third transducers configured to convert electrical signals into ultrasound energy and to transmit the ultrasound energy to the desired region, at least one frequency generator coupled to the first and second transducers and configured to supply electrical signals to the first and second transducers, a transmitter/receiver coupled to the third transducer and configured to provide pulse signals to the third transducer and to receive pulse echo signals from the third transducer, and a processor coupled to the transmitter/receiver and configured to analyze the pulse echo signals to determine at least one of amplitude, phase and frequency of vibration induced in the desired region by ultrasound energy transmitted by the first and second transducers, and to use the at least one of amplitude and frequency of the vibration to determine the property of the desired region.

Implementations of the invention may include one or more of the following features. The processor is configured to analyze the amplitude of the vibration and at least one of the frequency and the phase of the vibration. The at least one frequency generator is configured to provide the electrical signals to the first and second transducers with first and second frequencies, respectively, that are different from each other. The processor is configured to determine a value related to a mechanical property of the desired region. The value is proportional to a stiffness/elasticity of the desired region. The processor is configured to cross-correlate multiple received pulse echo signals.

In general, in another aspect, the invention provides a system of determining elasticity of a desired region in an object, the system including first and second ultrasound transducers configured to convert electrical signals into ultrasound energy and to transmit the ultrasound energy to the desired region, first and second frequency generators coupled to the first and second ultrasound transducers, respectively, and configured to provide the first and second ultrasound transducers, respectively, with first and second signals configured to cause the first and second ultrasound transducers to emit ultrasound energy having first and second frequencies, respectively, that are different, and determining means for providing energy to, and receiving energy from, the desired region and determining the elasticity of the desired region, based on the received energy, in a manner that is substantially independent of portions of the object disposed between the desired region and the system.

Implementations of the invention may include one or more of the following features. The determining means is configured to provide ultrasound pulses to the desired region, to detect echoes of the pulses, and to analyze the echoes of the pulses to determine at least one of amplitude and frequency of vibration induced in the desired region by the ultrasound energy transmitted by the first and second transducers. The determining means is configured to determine both the frequency and the amplitude of the vibration. The determining means is configured to cross-correlate multiple received echoes. The determining means comprises a third ultrasound transducer and wherein the first, second, and third ultrasound transducers are portions of a phased array of transducers. The first, second, and third ultrasound transducers each comprise a plurality of transducers. The first, second, and third transducers are part of one phased array and the third transducer is driven to produce an ultrasound beam with a frequency of about an odd harmonic frequency produced by other portions of the array.

Various aspects of the invention may provide one or more of the following advantages. A property, such as a mechanical property, of an object can be determined substantially uninfluenced by surroundings of the object. A mechanical property, such as elasticity/stiffness, of an object can be determined in a manner that is less dependent upon surroundings of the object than techniques that analyze spectral Doppler shift produced by the object's motion. A property of in vivo object can be determined in a manner that is substantially immune to noise and using a system that is compact. Tissue elasticity/stiffness at depths that a physician cannot reach can be determined. Tissue elasticity/stiffness can be monitored without using MRI. MR scanners can be used to obtain elasticity/stiffness information. The shear modulus, or stiffness, of tissues can be measured locally and deep inside tissue without having to mechanically alter surrounding tissue. Tissue response to a force-producing stimulus can be detected during application of the force. The shear modulus of tissue can be determined using a simple calculation. Elastic modulus variation in tissue, e.g., due to disease, can be measured. Highly sensitive differentiation of tissues based on their stiffness can be obtained. Accurate images for lesion localization can be obtained. Localized treatment, e.g., of tissue, can be performed and/or verified following the localization. Information regarding acoustic attenuation of tissue surrounding a targeted region may be obtained. Micron-level induced displacements of target regions can be estimated. Tissue elasticity/stiffness can be determined at variable depths with the precision provided by static techniques and the simplicity of harmonic excitation techniques.

These and other advantages of the invention, along with the invention itself, will be more fully understood after a review of the following figures, detailed description, and claims.

DETAILED DESCRIPTION OF PREFERRED EMBODIMENTS

Embodiments of the invention provide techniques for non-invasively detecting mechanical properties of tissues. For example, systems of the invention can detect tumors by determining tissue elastic modulus or stiffness (with stiffness and elasticity being related). To determine tissue elasticity/stiffness, multiple ultrasound sources transmit ultrasound beams of different frequencies into tissue such that the beams intersect at a desired location. The beams interfere with each other and produce a varying force in the tissue at the intersection. The force varies at a frequency equal to the difference of the frequencies of the beams, and causes the tissue at the intersection of the ultrasound beams to vibrate at the difference frequency. A third ultrasound source in the system sends a pulse or burst of ultrasound to the tissue at the intersection of the two beams. Echoes from reflections and scattering from the tissue due to the burst are measured. The amplitude and location of the echoes as a function of time provide information regarding the motion of the tissue and thus mechanical properties of the tissue at the intersection, in particular the elasticity/stiffness of the tissue at the intersection. The elastic modulus E and stiffness k are related to the frequency and magnitude of vibration of the tissue in the focal region, the ultrasound absorption coefficient of the tissue, the intensity of the ultrasound sources providing the intersecting beams, and the speed of sound. Multiple reflections are cross-correlated to determine the amplitude and frequency of the vibration of the tissue. Using some embodiments of the invention, elasticity/stiffness measurements may be made that are substantially immune to noise. Other embodiments are within the scope and spirit of the invention.

Figure 1:
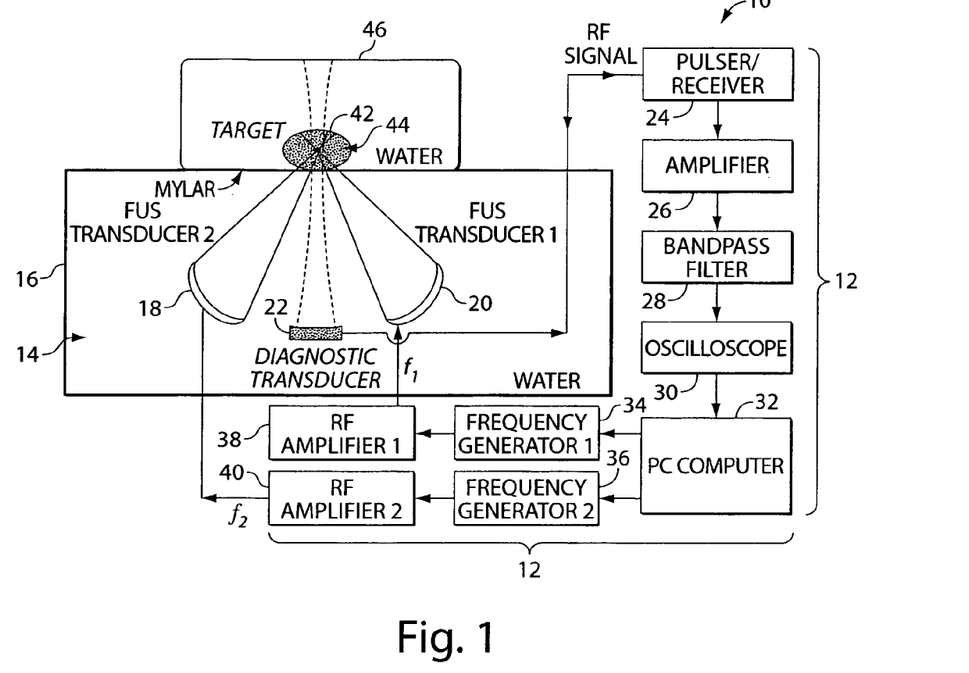
FIG. 1 is a simplified diagram of a localized harmonic motion imaging system.

Referring to FIG. 1, a localized harmonic motion imaging system 10 includes an ultrasound generator/receiver subsystem 12, a transducer set 14, and a tank (or other coupling technique) 16. The set 14 includes two focused ultrasound (FUS) transmitting transducers 18, 20, and a diagnostic transducer 22. The set 14 may be a phased array of transducers, with the transducers 18, 20 being portions of the phased array, that may be multiple transducers. The diagnostic transducer 22 may be implemented with one or more transducers, including being a portion of the phased array of which the transmitting transducers 18, 20 are part. The subsystem 12 includes a pulser/receiver 24, an amplifier 26, a bandpass filter 28, an oscilloscope 30, a personal computer 32, frequency generators 34, 36, and radio frequency (RF) amplifiers 38, 40. The system 10 is configured to image a subject 42 and more particularly a target region 44 in the subject 42. The tank 16 e.g., is filled with degassed water, and is separated from a target tank 46 containing the subject 42. A tank may not be used, e.g., in an in vivo case if coupling between the transducer and the subject is achieved.

The computer 32, the frequency generators 34, 36, and the RF amplifiers 38, 40 of the subsystem 12 are configured to provide excitation signals for the transducers 18, 20. The computer 32 is configured to drive the frequency generators 34, 36 to produce signals of frequencies $f_1$, $f_2$, respectively, that are in the RF range and that differ from each other. The amplifiers 38, 40 are configured to amplify the signals from the generators 34, 36 to produce the excitation signals for the transducers 18, 20.

The excitation signals provided by the subsystem 12 cause the transducers 18, 20 to produce RF ultrasound signals focused at the target 44 of the subject 42. Ultrasound beams from the transducers 18, 20 are directed to focus and intersect at the target 44 in the subject 42. Ultrasound produced by the transducers is at the frequencies $f_1$, $f_2$. These frequencies are different, e.g., each of about 0.5 and about 20 MHz with a difference $f_d = f_1 - f_2$ equal to from about 10 Hz to about 5000 Hz. This produces a radiation force $F_0$ in the target 44 at the frequency $f_d$, that results in tissue motion being produced. The tissue motion produced due to the vibration at the difference frequency $f_d$ is dependent upon various factors such as the mechanical and acoustical properties of the target region 44, The transducers 18, 20 are, manufactured such that they can produce adequate power output required for generating the tissue motion e.g. air backed transducers can be used. The subsystem 12 also provides pulse excitation signals for the diagnostic transducer 22. The pulser/receiver 24 operates the transducer 22 at a pulse/receive frequency, e.g., of about 0.5–20 MHz. For example, the transducer 22 may be driven to provide ultrasound at about an odd harmonic (e.g., third, fifth, etc.) of the set 14, e.g., if the transducers 18, 20, 22 are portions of the set 14, e.g., an array. The pulser/receiver 24 includes appropriate switching circuitry to selectively provide the transducer 22 (e.g., several adjacent transducers from the transducer array 14) with excitation pulses and to receive the RF-signals from the transducer 22. The pulser/receiver 24 is configured such that it can cause the transducer 22 to send the ultrasound pulses/bursts toward the target region 44 while the transducers 18, 20 are transmitting energy beams to the target region 44. Preferably, the transducer 22 comprises enough transducers from the set 14 to provide a well-collimated or focused beam to the target region 44. A variety of transducers may be used for the transducer 22, e.g., a transducer commonly used for diagnostic purposes and for example a custom-made PZT composite transducer. The diagnostic transducer 22 is also aimed at the target 44 of the subject 42 such that the pulses provided by the transducer 22 are incident upon the target region 44 that is vibrating at the difference frequency $f_d$. It has been discovered that echoes as a function of time from the target 44 due to the pulses/bursts from the diagnostic transducer 22 provide information regarding the tissue motion and thus mechanical properties of the target 44 substantially independently of the surroundings of the target 44. Also, it has been discovered that comparing measured reflections may help dissociate attenuation effects from the mechanical effects of different targets, e.g., tissues.

Portions of the subsystem 12 are configured to receive and process the echoes from the target 44. The pulser/receiver 24 is configured to detect the echoes, produce RF signals in response to the echoes, and pass the responses to the amplifier 26. The amplifier 26 amplifies the received signals and provides the amplified signals to the bandpass filter 28. The bandpass filter 28 is configured to inhibit and/or substantially block the fundamental frequency of the radiation-force-producing transducers 18, 20 and its harmonics. The signals that pass through the filter 28 are digitized by a high speed digital converter, here the oscilloscope 30, e.g., a DL 7100 digital oscilloscope made by Yokogawa of Tokyo, Japan. The digitized data are stored, e.g., on a disk for analysis by the controller 32. The computer 32 is preferably configured to control selection of the transducers from the array 14 for use as the transducer 22. For ultrasound imaging purposes, the transducer array selected elements can be shifted by one to produce RF signals and the pulse repeated. This may be repeated for all elements of the array 14 and the resulting data used to produce a B-scan of the whole imaging plane as a separate feature of the array 14.

Figure 2:
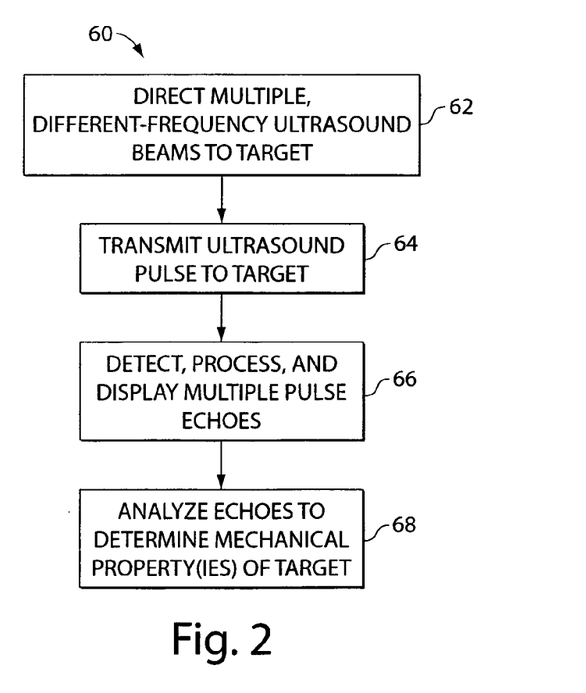
FIG. 2 is a block flow diagram of a process of determining mechanical properties using the system shown in FIG. 1.

The computer 32 is configured to process the received, amplified, filtered, and digitized reflected signals to determine the mechanical elasticity/stiffness of the target 44. The computer 32 performs RF signal tracking using crosscorrelation techniques with a window on the order of 1–2 mm. This window represents a signal length (or duration) to be crosscorrelated before and after motion has occurred and has been found to be sufficient to produce precise time delay, or displacement, estimates. This signal duration corresponds to approximately 2 mm travel by the ultrasound pulse in the tissue. The computer 32 estimates displacement of the target 44 relative to the target's initial position (i.e., before application of the radiation force) during the application of the radiation force. The computer 32 also images the target 44 in an M-mode-like (motion-mode-like) fashion to determine the spatial and temporal variation of the target 44. Thus, the target 44 is imaged over time to show its motion. Using the crosscorrelated information to show displacement over time, the computer 32 determines magnitude and frequency of the target's displacement. Referring to FIG. 2, the computer 32 can image the received signals from the diagnostic transducer 22 over time to determine displacement of the target 44 over time. This yields magnitude and frequency information regarding the displacement of the target 44 due to the excitation signals from the transducers 18, 20. From the displacement information, the computer 32 can estimate the elastic modulus E of the target 44 according to:

$$E = 2(1-v^2)F_0 r / X_0 A \qquad (1)$$

where $$F_0 = \frac{2\alpha I}{c} \qquad (2)$$

where $F_0$ is the applied radiation force, r is the tissue radius, v is Poisson's ratio, A is the tissue area in motion, $f_0$ and $X_0$ are the frequency and magnitude, respectively, of vibration, e.g., of tissue, in the target focal region 44, $\alpha$ is the ultrasound absorption of the propagating wave by the target 44, I is the intensity of the ultrasound transducers 18, 20 providing the intersecting beams, and c is the speed of sound. The absorption is frequency dependent and is typically expressed in units of Np/cm/MHz, and for soft tissue is usually assumed to be the tissue attenuation.

In operation, referring to FIG. 2, with further reference to FIG. 1, a process 60 for determining tissue elasticity/stiffness using the system 10 includes the stages shown. The process 60, however, is exemplary only and not limiting. The process 60 may be altered, e.g., by having stages added, removed, or rearranged.

At stage 62, two ultrasound beams are directed to the target 44. The computer 32 controls the frequency generators 34, 36 to produce signals at the frequencies $f_1$ and $f_2$, respectively. These signals are amplified by the amplifiers 38, 40 and supplied to the radiation force generating transducers 20, 18, respectively. The transducers 18, 20 convert the received electronic signals into ultrasound and transmit the ultrasound of intensity I toward, and focused at, the target region 44 of the subject 42. This induces motion in the target region at the difference frequency $f_d = f_1 - f_2$.

At stage 64, a pulse is produced and transmitted to the target region 44. The pulser/receiver 24 sends an electronic signal to the diagnostic transducer 22. This pulse can, and preferably is, provided while the two beams of frequencies $f_1$, $f_2$ are inducing motion of the target region 44. The transducer 22 converts this into an ultrasound pulse and sends the pulse to the target region 44. The pulse reflects off of the target region 44 to produce an echo received at the same transducer.

At stage 66, multiple echoes are detected, processed, and displayed. The echoes are received by the diagnostic transducer 22, converted to electrical signals and sent to the puler/receiver 24. These electrical echo signals are passed to the amplifier and the bandpass filter where they are amplified and filtered. The amplified, filtered echo signals are displayed by the oscilloscope 30.

Figure 3:
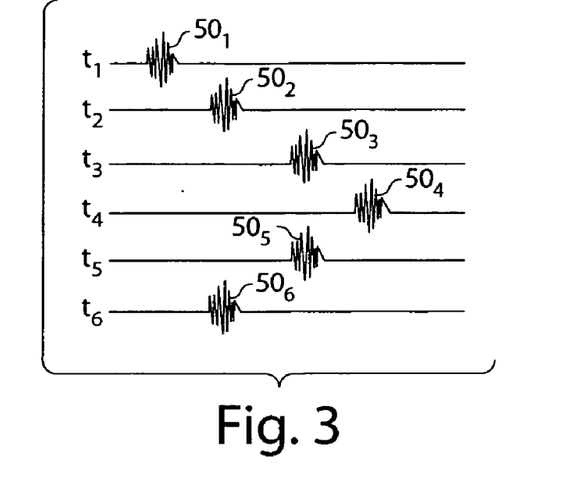
FIG. 3 is a diagram of pulse reflections received over time.
Figure 4:
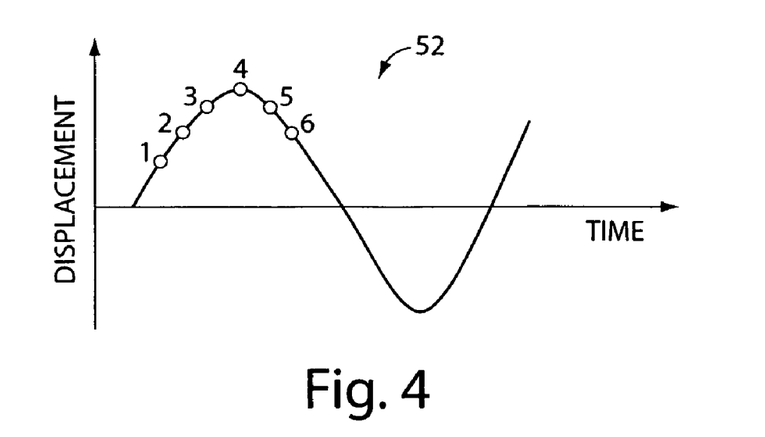
FIG. 4 is a diagram showing vibration displacement of a target region over time.
Figure 5A:
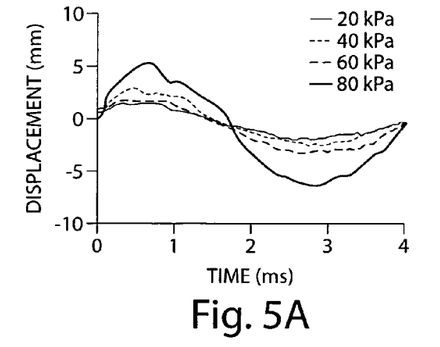
FIGS. 5A–5D are plots of finite-element simulations of displacement of targets of varying stiffness in response to different frequencies of radiation forces.
Figure 5B:
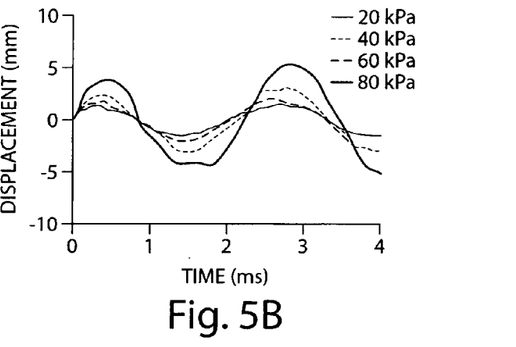
Figure 5C:
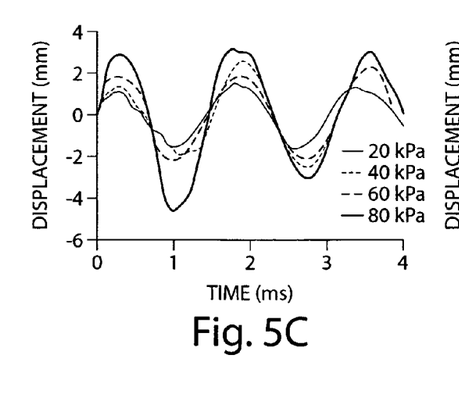
Figure 5D:
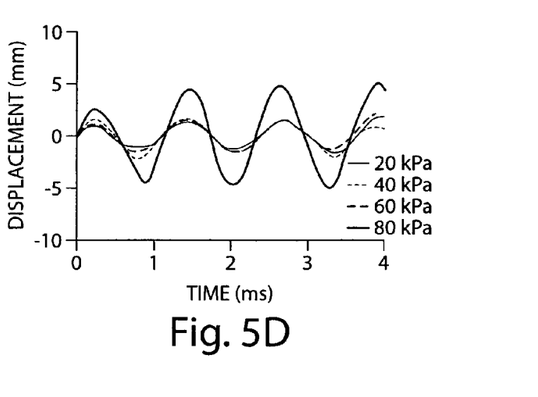

At stage 68, the echo signals are analyzed by the computer 32 to determine one or more mechanical responses or properties of the target region 44. The computer 32 determines displacement values for the target region over a period of time with a certain number N of echoes received. Referring to FIG. 3, six pulses are sent at six (N=6) different times $t_1-t_6$. Echoes $50_1-50_6$ are received by the subsystem 12 at different times and from these times the computer 32 can determine the displacement of the target region 44 at the times $t_1-t_6$. The computer 32 can cross-correlate the echoes 50 by making a plot 52 of the echoes 50 over time as shown in FIG. 4. In FIG. 4, the six designated points correspond to the determined displacements at the six times $t_1-t_6$. The plot 52 represents the vibration amplitude of the target region 44. By analyzing characteristics of the plot 52, e.g., the peaks, troughs, and/or zero crossings for relevant data, such as magnitudes and/or timing of peaks/troughs and/or timing of zero crossings, the computer 32 can determine the magnitude $X_0$ and frequency $f_0$ of the target region's vibration. By using the target region's absorption α (known or measured) and the known intensity I of the FUS transducers 18, 20 in equation (2), the computer 32 calculates the radiation force $F_0$. By inserting the determined radiation force $F_0$, the magnitude $X_0$, and the frequency $f_0$ into equation (1), the computer 32 determines the elastic modulus E of the target region 44.

Non-invasively determining tissue elasticity/stiffness, or relative tissue elasticity/stiffness, or relative tissue motion amplitude or frequency shift map (e.g., if elasticity/stiffness cannot be determined) lends itself readily to several applications, including diagnosis and therapy. For diagnosis, the elasticity/stiffness of tissues of the subject 42 may be determined. Determining elasticity/stiffness of the target region 44 and of surrounding tissue may help to identify and diagnose tumors or other irregular or abnormal entities in the subject 42. Indeed, it may be possible to determine specific tumor types based upon an elasticity/stiffness value. Thus, different tumor types could be differentiated non-invasively based upon their respective elasticity and/or stiffness values. Further, for therapy, the FUS transducers 18, 20 may have high intensities such that the ultrasound from the transducers 18, 20 induces coagulation of tissue in the target region 44. The system 10 may be used to determine elasticity/stiffness change of the target region 44 to thereby confirm coagulation of the tissue in the target region 44. This may eliminate the need for MR imaging, as presently used, of temperature for ultrasound therapy of this nature. Embodiments of the invention may also be used to perform local harmonic motion imaging to guide, monitor, and/or control thermal treatments. Other applications are within the scope of the invention. Relative elasticity/stiffness determinations may also be used to locate targets. By knowing the difference in elasticity/stiffness between two regions, surrounding tissue (e.g., healthy breast or brain tissue) can be differentiated from other tissue (e.g., a tumor) so that a target for treatment such as ablation may be located.

Experimental and Simulated Data

Figure 6A:
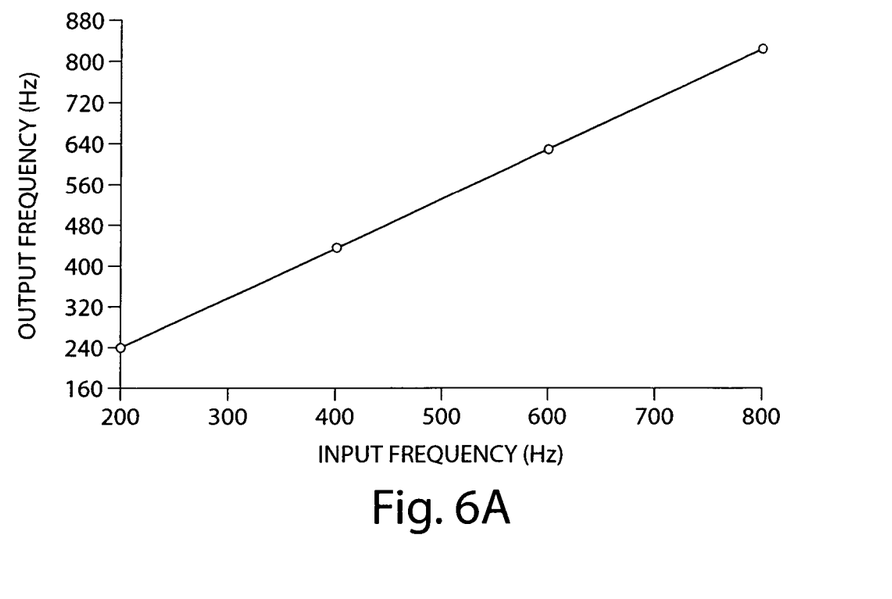
FIG. 6A is a plot of input radiation force frequency versus simulated target vibration frequency.
Figure 6B:
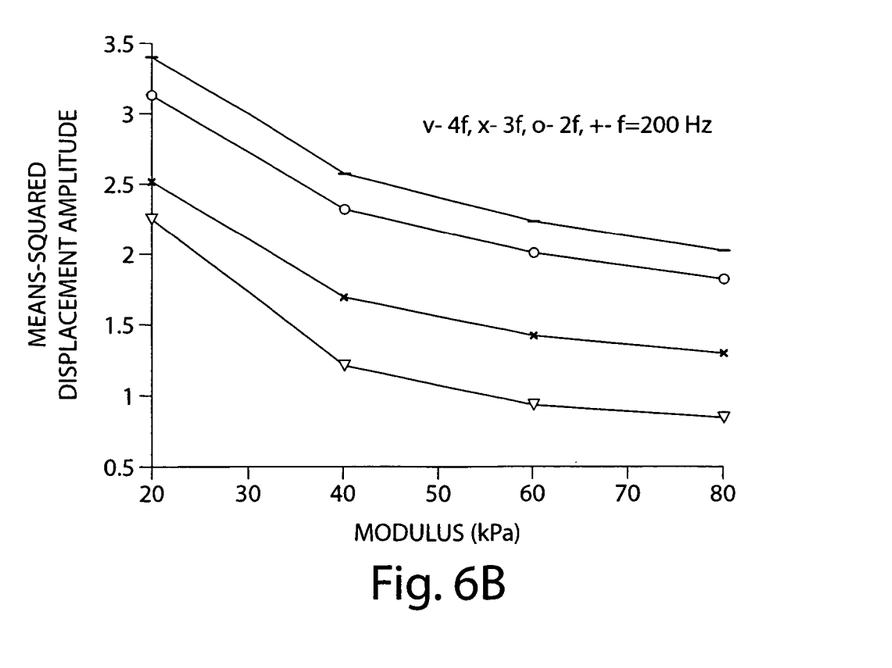
FIG. 6B is a plot of stiffness versus simulated target displacement for various input radiation force frequencies. input radiation force frequencies.
Figure 7A:
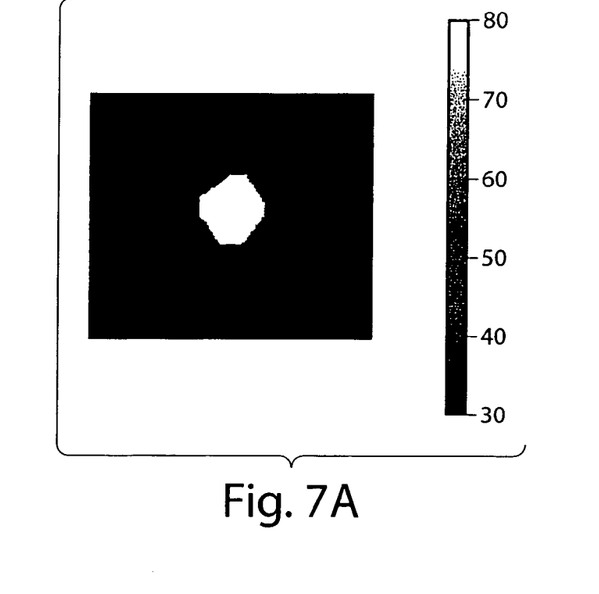
FIGS. 7A–7B are true modulus and estimated displacement images of a target.
Figure 7B:
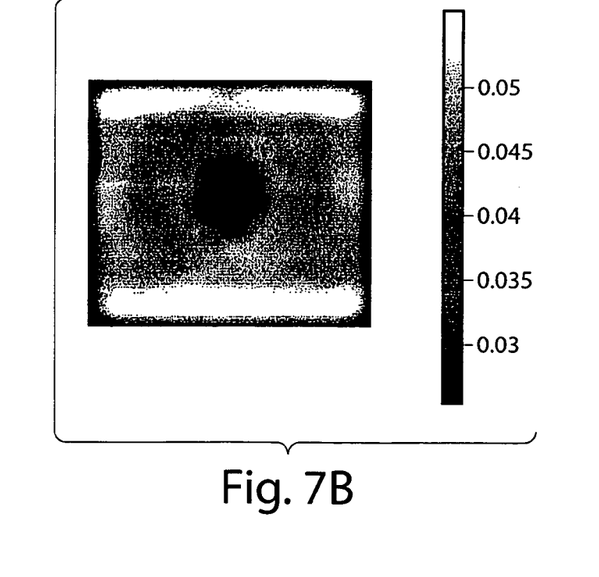

To evaluate parameters (e.g., loading frequency and tissue modulus) to be used with techniques according to the invention, finite-element simulations and a signal generation model for RF signal simulation were used. To model tissues containing tumors, finite-element simulations of mechanical targets that contain inclusions of distinct stiffness from the surrounding medium were considered. The "normal" tissue had a stiffness of 30 kPa and the "tumorous" tissue varied from 30 kPa to 500 kPa in stiffness. Referring to FIGS. 5A–5D, displacement plots at each of four difference frequencies $f_d$ of 200 Hz, 400 Hz, 600 Hz, and 800 Hz for tissue stiffness of 20 kPa, 40 kPa, 60 kPa, and 80 kPa show that the vibration frequency increases with increasing stiffness and the vibration magnitude decreases with increasing stiffness. The decrease in displacement magnitude is exponential, and occurred at all of the selected frequencies, according to the simulations. The frequency shift with changing stiffness is reflected in the number of cycles in the displacement plot consistently decreasing as stiffness increases. FIGS. 6A and 6B summarize findings from the simulations, with FIG. 6A showing vibration frequency $f_0$ of the target 44 vs. applied difference frequency $f_d$ and FIG. 6B illustrating changing displacement magnitude $X_0$ with changing module E for various difference frequencies $f_d$. FIG. 7A shows a true modulus of a tumor and FIG. 7B shows a simulated image according to the displacement magnitude $X_0$.

Figure 8:
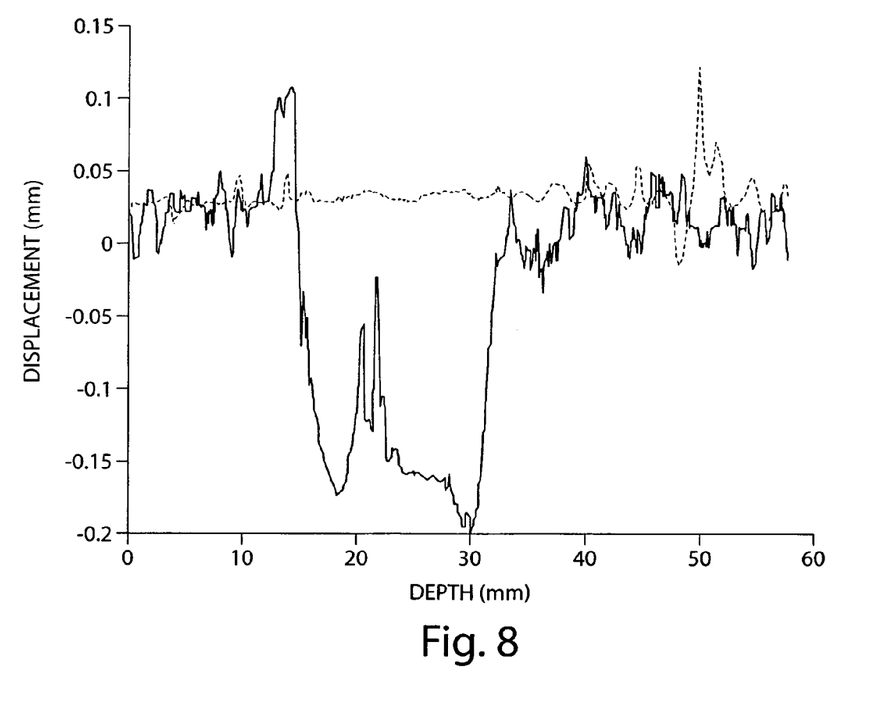
FIG. 8 is a plot of experimental target displacement versus depth before and during harmonic motion excitation.
Figure 9A:
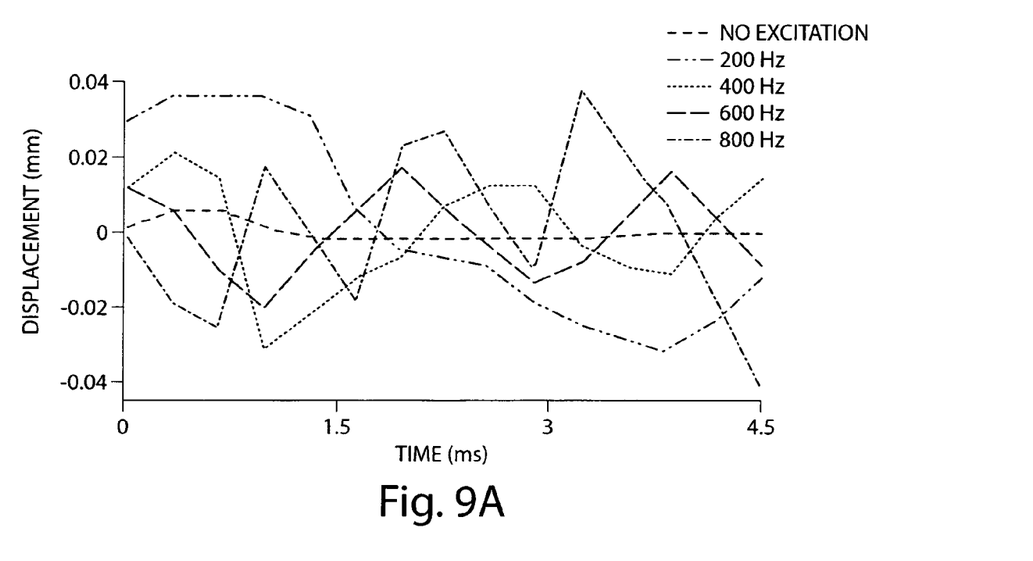
FIGS. 9A–9B are plots of experimental target displacement versus time for a target of modulus 25.9 kPa for excitation frequencies of 0 Hz, 200 Hz, 400 Hz, 600 Hz, and 800 Hz (9 A), and for targets of modulus 7.1 kPa, 25,9 kPa, 55.2 kPa, and 94.6 kPa at an excitation frequency of 800 Hz.
Figure 9B:
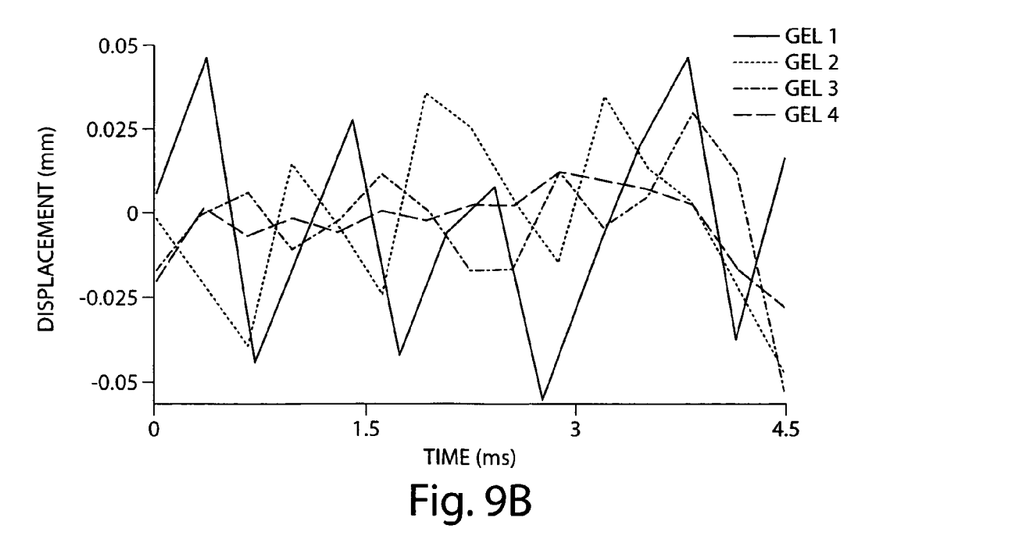
Figure 10:
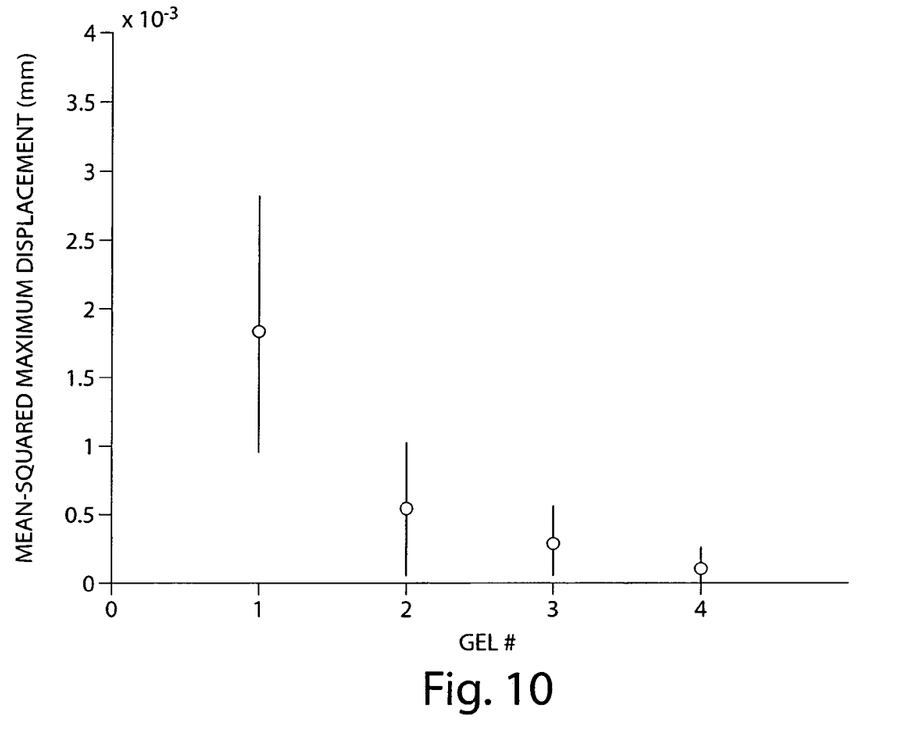
FIG. 10 is a plot of experimental displacement for four targets of varying stiffness.

An embodiment of the invention was tested on agar gel phantoms using Sigma agar powder embedded with glass beads. The beads were about 71 microns in diameter and were added for scattering purposes. The gel phantoms had moduli of 7.1 kPa (Gel 1), 25.9 kPa (Gel 2), 55.2 kPa (Gel 3), and 94.6 kPa (Gel 4). The applied radiation force oscillated at frequencies from about 100 Hz to about 800 Hz and estimates of the displacement relative to the initial position (at the onset of the application of the radiation force) were obtained during application of the radiation force. FIG. 8 shows the spatial distribution of displacement profiles before and during harmonic motion excitation. The focal spot at which motion is induced can clearly be seen in FIG. 8 to occur between 15 and 23 mm. FIGS. 11A-11B summarize results obtained with the gels. As shown in FIG. 11A, the displacement frequency of Gel 2 is the same as the applied radiation force frequency for frequencies of 200 Hz, 400 Hz, 600 Hz, and 800 Hz. As shown in FIG. 11B, the displacement amplitude decreased with increasing stiffness of the gels under a radiation force frequency of 800 Hz. FIG. 10 summarizes results from the four gels using a radiation frequency of 800 Hz. The error bars in FIG. 10 represent one standard deviation obtained from three independent locations in each gel. The displacement amplitude decreased with stiffness, similar to the results observed with the simulations.

Figure 11:
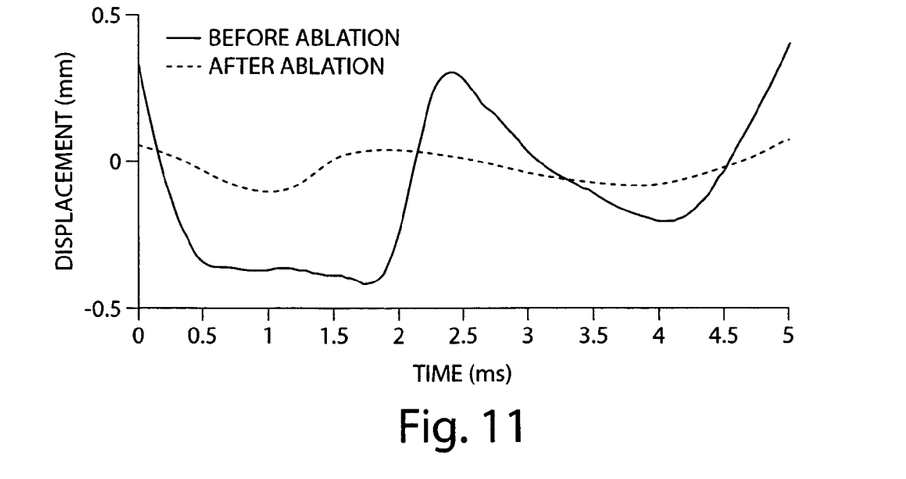
FIG. 11 is a plot of experimental displacement versus time before and after ablation of a target in porcine muscle.

Experiments were also performed on porcine thigh muscle to determine target vibration before and after coagulation using focused ultrasound. FIG. 11 shows the displacement of the porcine tissue at a depth of 21 mm before and after ablation. As shown, before coagulation the tissue vibrated at a depth of 21 mm while after ablation the tissue no longer underwent the same amplitude of harmonic displacement at 21 mm.

Other embodiments are within the scope and spirit of the appended claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. Further, finite-element simulations showed a shift in the induced displacement frequency that varied with stiffness. In particular, referring to FIGS. 5A–5D, a frequency shift with stiffness change (on the order of tens of Hz) was estimated with stiffness increase. Equation (1) may be modified to help compensate for this frequency shift, although good correlation between estimated and actual elasticity/stiffness values were obtained without compensating for this frequency shift. Further, the simulations and experiments showed an exponential decrease of the displacement amplitude with stiffness. This effect may also be accounted for in equation (1).

What is claimed is:

1. A method of determining a property of a desired region in an object, the method comprising:
    transmitting first and second focused ultrasound energy beams from first and second sources into the object such that the focused ultrasound beams intersect at the desired region to induce vibration of the desired region by providing a pushing force to the desired region;
    transmitting a third focused ultrasound energy beam from a third source into the desired region;
    receiving echo signals from the desired region indicative of reflected energy from the third source; and
    analyzing at least one of amplitude, phase and frequency of the vibration of the desired region indicated by the received signals by correlating indicia of values of the received signals at different times to determine the property of the desired region.

2. The method of claim 1 wherein the analyzing comprises analyzing the amplitude of the vibration and at least one of the frequency and the phase of the vibration.

3. The method of claim 2 wherein the first and second energy beams have first and second frequencies, respectively, that are different from each other.

4. The method of claim 2 wherein the analyzing determines a value related to a mechanical property of the desired region or a parameter that is related to the mechanical property of the desired region.

5. The method of claim 4 wherein the value is related to a stiffness/elasticity of the desired region.

6. The method of claim 2 wherein the analyzing comprises cross-correlating multiple received signals.

7. The method of claim 6 wherein the energy from the third source is one of a plurality of ultrasound pulses and a plurality of ultrasound bursts.

8. A system for determining a property of a desired region in an object, the system comprising:
    first, second, and third transducers configured to convert electrical signals into focused ultrasound energy and to transmit the focused ultrasound energy to the desired region to induce a pushing force on the desired region;
    at least one frequency generator coupled to the first and second transducers and configured to supply electrical signals to the first and second transducers;
    a transmitter/receiver coupled to the third transducer and configured to provide ultrasound pulse signals to the third transducer and to receive ultrasound pulse echo signals from the third transducer; and
    a processor coupled to the transmitter/receiver and configured to analyze the ultrasound pulse echo signals to determine at least one of amplitude, phase and frequency of vibration induced in the desired region by the pushing force provided by the focused ultrasound energy transmitted by the first and second transducers, and to use the at least one of amplitude and frequency of the vibration to determine the property of the desired region.

9. The system of claim 8 wherein the processor is configured to analyze the amplitude of the vibration and at least one of the frequency and the phase of the vibration.

10. The system of claim 9 wherein the at least one frequency generator is configured to provide the electrical signals to the first and second transducers with first and second frequencies, respectively, that are different from each other.

11. The system of claim 9 wherein the processor is configured to determine a value related to a mechanical property of the desired region.

12. The system of claim 9 wherein the value is proportional to a stiffness/elasticity of the desired region.

13. The system of claim 9 wherein the processor is configured to cross-correlate multiple received pulse echo signals.

14. A system of determining elasticity of a desired region in an object, the system comprising:
    first and second ultrasound transducers configured to convert electrical signals into focused ultrasound energy and to transmit the focused ultrasound energy to provide a pushing force to induce vibration of the desired region;
    first and second frequency generators coupled to the first and second ultrasound transducers, respectively, and configured to provide the first and second ultrasound transducers, respectively, with first and second signals configured to cause the first and second ultrasound transducers to emit focused ultrasound energy having first and second frequencies, respectively, that are different; and
    determining means for providing focused ultrasound energy to, and receiving reflected ultrasound energy from, the desired region and determining the elasticity of the desired region, based on the received reflected energy, in a manner that is substantially independent of portions of the object disposed between the desired region and the system.

15. The system of claim 14 wherein the determining means is configured to provide ultrasound pulses to the desired region, to detect echoes of the pulses, and to analyze the echoes of the pulses to determine at least one of amplitude and frequency of vibration induced in the desired region by the pushing force of the focused ultrasound energy transmitted by the first and second transducers.

16. The system of claim 15 wherein the determining means is configured to determine both the frequency and the amplitude of the vibration.

17. The system of claim 16 wherein the determining means is configured to cross-correlate multiple received echoes.

18. The system of claim 17 wherein the determining means comprises a third ultrasound transducer and wherein the first, second, and third ultrasound transducers are portions of a phased array of transducers.

19. The system of claim 18 wherein the first second, and third ultrasound transducers each comprise a plurality of transducers.

20. The system of claim 18 wherein the first, second, and third transducers are part of one phased array and the third transducer is driven to produce an ultrasound beam with a frequency of about an odd harmonic frequency produced by other portions of the array.

* * * * *